United States Patent [19]

Thorne et al.

[11] Patent Number: 5,401,659
[45] Date of Patent: Mar. 28, 1995

[54] BIOLOGICALLY PURE CULTURE OF BACILLUS ATCC 55294 THAT PRODUCES AN ENDOGLYCANASE

[75] Inventors: Linda P. Thorne, Palomar; Richard W. Armentrout, La Jolla; Thomas J. Pollock, San Diego; Marcia J. Mikolajczak, Encinitas, all of Calif.

[73] Assignees: Shin-Etsu Bio, Inc., San Diego, Calif.; Shin-Etsu Chemical Co., Ltd., Tokyo, Japan

[21] Appl. No.: 251,600

[22] Filed: May 31, 1994

Related U.S. Application Data

[60] Division of Ser. No. 16,357, Feb. 11, 1993, Pat. No. 5,342,773, which is a continuation-in-part of Ser. No. 837,822, Feb. 18, 1992, abandoned.

[51] Int. Cl.⁶ .................. C12N 9/24; C12N 1/20; C12N 1/00; C12P 19/14
[52] U.S. Cl. .................. 435/252.5; 435/200; 435/832; 435/18; 435/99; 435/104
[58] Field of Search ............ 435/252.5, 200, 832, 435/18, 99, 104

[56] References Cited

U.S. PATENT DOCUMENTS

| | | | |
|---|---|---|---|
| 4,342,866 | 8/1982 | Kang et al. | 536/119 |
| 4,963,668 | 10/1990 | Allen et al. | 536/114 |
| 5,004,506 | 4/1991 | Allen et al. | 106/729 |
| 5,015,470 | 5/1991 | Gibson | 424/70 |
| 5,068,186 | 11/1991 | Schlingmann et al. | 435/96 |

OTHER PUBLICATIONS

Datton et al., Biomedical & Environmental Mass Spectrometry, vol. 15, 459–60, 1988.
Acebes et al., Physiologia Plantarum, 86: 433–439, 1992.
Parolis et al., Carbohydrate Research, 31, 93–103, 1992.
Elyakova et al., Molecular Biology (Russia), vol. 16, No. 3, Part 1, Nov. 1982, pp. 393–403.
Chowdhary et al., Carbohydrate Research, 164, 1987, pp. 117–22.
Bio/Technology Nov. 1983–pp. 778–783 (1983)–Baird, Sanford and Cottrell–"Industrial Applications of some new Microbial Polysaccharides".
Carbohydrate Research, 139–pp. 217–223 (1985)–Jansson, Lindberg and Widmalm–"Structural Studies of an Extracellular Polysaccharide (S-130) elaborated by *Alcaligenes* ATCC 31555".
Dev. Ind. Microbial. 26–pp. 281–289 (1985)–Cadmus and Slodki–"Enzymic breakage of Xanthan Gum Solution viscosity in the presence of salts–using Xanthan Gum degrading enzyme complex from *Bacillus* sp.".
Canadian J. Microbial. 35 pp. 559–564 (1989)–Casida, Jr.–"*Arthrobacter* species as prey cell reservoir for nonobligate bacterial predators in soil".

*Primary Examiner*—David M. Naff
*Assistant Examiner*—Mike Meller
*Attorney, Agent, or Firm*—McAulay Fisher Nissen Goldberg & Kiel

[57] ABSTRACT

An isolated endogly canase having activity against polysaccharides having the subunit backbone structure:

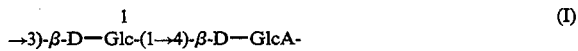

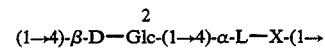

wherein Glc is glucose, GlcA is glucuronic acid, Rha is rhamnose, Man is mannose, X may be Rha or Man, and wherein the reducing end of the polymer is toward the X residue of the backbone is disclosed. A method for producing the compound by culturing Bacillus ATCC 55294, the method for selecting Bacillus ATCC 55294 and method for using the endoglycanase are also disclosed.

7 Claims, No Drawings

BIOLOGICALLY PURE CULTURE OF BACILLUS ATCC 55294 THAT PRODUCES AN ENDOGLYCANASE

This is a Division of application Ser. No. 08/016,357, filed Feb. 11, 1993, now U.S. Pat. No. 5,342,773, which, in turn, is a Continuation-In-Part of Ser. No. 07/837,822, filed Feb. 18, 1992, abandoned.

BACKGROUND OF THE INVENTION

Welan or S-130 is a carbohydrate polymer secreted into the culture medium by a species of gram-negative bacteria, named *Alcaligenes* (See U.S. Pat. No. 4,342,866). It is a member of a polysaccharide family having the subunit backbone of the general structure I:

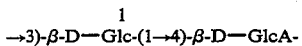
(I)

wherein Glc is glucose, GlcA is glucuronic acid, Rha is rhamnose, Man is mannose, X may be Rha or Man, and wherein the reducing end of the polymer is toward the residue X. This structure (I) is sometimes referred to herein as the "backbone". Various side chains may be attached to the backbone.

Typically members of this polysaccharide family have the general repeating structure II:

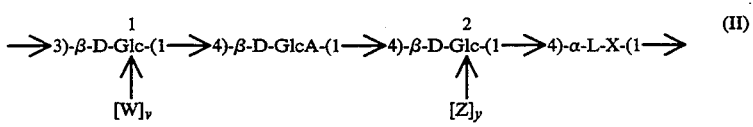

wherein Glc is glucose; GlcA is glucuronic acid; Rha is rhamnose; Man is mannose; X may be Rha or Man; Z may be α-L-Rha-(1→6)-α-L-Rha, α-L-Man, α-L-Rha, or Glc; W may be β-D-Glc-(1→6)-α-D-Glc or α-L-Rha, subscripts v an y may be either 0, 0.5, or 1, and wherein the reducing end of the polymer is toward the X residue of the backbone. As used herein, the expression "backbone" refers to that portion of structure I which excludes chains W and Z, i.e., when v and y are equal to 0.

Some members of this family of polysaccharides are acetylated at various positions. However, the polysaccharides may be subjected to chemical deacylation in a conventional manner to remove the acyl groups. For example, gellan is a carbohydrate polymer secreted into culture medium by *Pseudomonas elodea* (ATCC 31461). Gellan has the same carbohydrate backbone as welan (i.e., X=Rha), but lacks the side chain sugar (i.e. v=O and y=O) and the glucose residue 1 is fully substituted with glycerate. The gellan subunit structure is also acylated at unknown positions. Chemical deacylation of gellan produces a polymer which forms a clear gel in the presence of cations. This processed form of gellan is available commercially under the name Gelrite TM and is used as an agar substitute for culturing microorganisms and plants.

The gellan family of microbial polysaccharides includes at least seven different polymers which have very similar or identical backbone structures (shown in Table 5 hereinafter in abbreviated form). The known members of this family include: gellan (also called polysaccharide S-60), welan (S-130), S-88, rhamsan (S-194), S-657, S-198, and NW11. All have either gel forming properties or form highly viscous aqueous solutions which make them candidates for commercial applications. However, it is difficult and time consuming to evaluate newly isolated polysaccharides and determine whether or not the new polymer is a member of the gellan family of polysaccharides.

Welan has the following repeat structure III (Jansen, P. -E., Lindberg, B., Widmalm, G. and Sandford, P. A., 1985; *Carbohydrate Research* 139: 217–223):

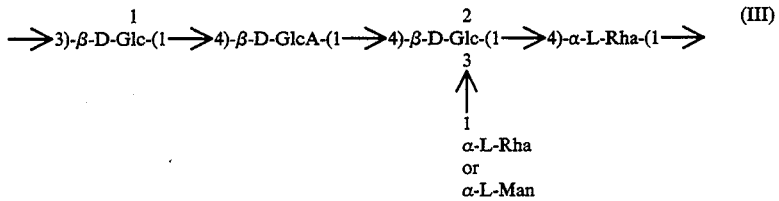

wherein Glc is glucose; ClcA is glucuronic acid; Rha is rhamnose; and Man is mannose.

As shown above, a side chain composed of either a single mannose or rhamnose sugar is linked to the tetrasaccharide backbone subunit at the glucose residue "2". Although this polymer is negatively charged, due to glucuronic acid residues in the polymer backbone, the polymer is compatible with portland cement. Welan has been proposed as a cement additive because of its strong suspending properties and its ability to reduce entrained air in the cement and to control water loss. See U.S. Pat. Nos. 4,963,668 and 5,004,506. However, for several applications, the native polymer imparts an undesirable high viscosity to the cement.

Methods for chemical cleavage of welan to reduce its viscosity are disclosed in U.S. Pat. Nos. 4,963,668 and 5,004,506. However, the chemical cleavage effected by this method leads to random degradation of the polymer chain and its sugar moieties resulting in a nonuniform chemical composition. This process uses a nonspecific oxidation reaction using Fenton's reagent. In order to reduce the amounts of chemicals needed (especially hydrogen peroxide), the patent suggests that the broth be treated first with protease. In addition, the fermentation broth must be heated to about 60° C. (from the fermentation temperature of about 30° C.). Ferrous sulfate (0.05%) and EDTA (a chelation agent, 0.1%) are added first as essential catalysts. Then hydrogen peroxide is added over a 1 to 3 hour period to a final concentration of 0.1.5 to 0.25%. When the broth viscosity is reduced to about 80 to 100 cp, the broth is cooled to about 27° C. and is neutralized with KOH. Welan is recovered by precipitation with isopropyl alcohol.

Viscous solutions of welan are stable in high concentrations of salt and at high temperatures. Because of this stability, welan could be a candidate for oil field applications, since high viscosity fluids are used as suspending agents for hydraulic fracture during well completion. See Baird, J. K., P. A. Sandford and I. W. Cottrell, 1983, *Bio/technology*:778–783). However, after well completion, it is necessary to reduce the viscosity of the fluids to allow stimulated flow of oil or gas. The prior art processes described above make it difficult and/or expensive to accomplish this with welan.

The use of xanthan gum for hydraulic fracture fluids is known. Specific enzymes are available to reduce the viscosity of xanthan gum, and it has been proposed that these enzymes be used to reduce the viscosity of Xanthan gum-containing fracture fluids (Cadmus, M. C. and M. E. Slodki, 1985; *Developments in Industrial Microbiology* 26:281–289).

SUMMARY OF THE INVENTION

We have discovered a new compound which exhibits enzyme activity and which specifically cleaves the backbone structure of members of the gellan family of polysaccharides having structure I and a method for making and concentrating the compound into a useful form. We have further discovered a method for decreasing the viscosity of solutions of these polysaccharides using the inventive compound as well as the decreased viscosity digestion products produced thereby. These lower molecular weight compositions are useful, for example, in oil field applications, as cement additives, and the like. Their manner of use are the same as for the polysaccharides described above, e.g., xanthan.

The inventive compound is produced by utilizing an inventive selection method to obtain a biologically pure strain of *Bacillus* specie which produces the compound under submerged culture conditions in the presence of a polysaccharide of structure I and separating the product from the fermentation broth.

In addition, we have found a method for the rapid and specific detection of polysaccharides having structure I using the inventive compound. The enzymatic cleavage effected by the present invention is highly selective for specific carbohydrate bonds. The inventive cleavage process avoids the complexity and the need to add the environmentally adverse and/or difficult-to-handle or hazardous chemicals required by the prior an chemical treatments. In addition, residues of these chemicals in the product can be avoided and the process can be carried out at relatively low temperatures, e.g., temperatures about the same as the fermentation. Also, the polymer size can easily be controlled by limiting the extent of the digestion.

DETAILED DESCRIPTION OF THE INVENTION

In the inventive selection method, a naturally occurring source of a collection of bacteria, e.g., soil, leaves, bark, plant life, etc., are treated to enrich the presence of bacteria able to utilize polysaccharides of structure I. This is achieved by cultivating such a collection, e.g., in a soil sample, in a medium wherein the polysaccharide of structure I is the predominant or only carbon source. As used herein, the expression "predominant carbon source" means that the polysaccharide referred to is present to the substantial exclusion of other carbon sources which could sustain bacteria unable to utilize polysaccharides having the backbone of structure I.

In practice, the polysaccharide sources commercially available often are not pure in that they contain contaminants, e.g., bacterial debris, which can also be utilized as a carbon source. As a result, after the enrichment step, the collection of enriched bacteria is further purified by culturing in a medium (gel) which contains as a predominant carbon source, substantially uncontaminated polysaccharide having structure I. It is preferable that the carbon source be free, not only, of cellular debris, but also, from side chains, i.e., carbohydrate chains attached to the backbone. Since it is desired to cultivate the growth of bacteria which act endolytically, i.e., attack the backbone of the polymer, it is best to avoid side groups which may support non-endolytic bacteria. Typical of such materials is Gelrite ™, which has no side chains, but does possess the backbone of structure I.

Typically, the enriched bacteria collection is cultured on gel media containing a polysaccharide having structure I, preferably, without the side chain, i.e. wherein $y=0$ and $v=0$. Colonies which grow under these conditions and which create a visibly detectable depression or pitting in the gel are selected for further purification, e.g., as by repeated culturing, or used as is. It is important the pitting be observed since it is an indication that the bacteria are dissolving the gel or cleaving it into fragments which is a sign of endolytic digestion.

If it is desired to digest a compound having structure I wherein side chains are present, then an additional screening step is employed. In this step, the selected strain of bacteria is subjected to submerged liquid culture in the presence of the particular polysaccharide which should represent the predominant carbon source in the medium. By monitoring the viscosity of the product, it can be determined that the organism is producing a product having the desired endolytic properties. Thus, if a relatively large and rapid viscosity decrease is observed, it is reasonable to conclude that endolytic cleavage is taking place. On the other hand, a relatively gradual viscosity decrease over a longer time period indicates that exolytic cleavage at the ends of the backbone is occurring.

Accordingly, the inventive compound provides a facile means for rapid screening of polysaccharides to determine if these structural determinants are present. This is accomplished by simply subjecting the polysaccharide to digestion conditions with the inventive compound and testing the product mixture for a viscosity decrease.

More particularly, a viscous aqueous solution of the polymer to be studied is prepared. The concentration of polymer is adjusted to give a viscosity which is high relative to water, but conveniently measured in a viscometer, for example, about 100 cp using the #18 spindle attachment in a LVTD-VII Brookfield viscometer. The aqueous solution may be buffered with a convenient buffer (0.01 to 0.02 M sodium phosphate buffer, pH about 7, for example). The polymer solution need not be pure, i.e., it can contain bacterial debris and even other, minor polymer structures in addition to the polymer under analysis, which should not contribute much of the viscosity. Also, the solution may contain chemicals to prevent the growth of bacteria, i.e., 0.01% sodium azide.

A solution of the inventive compound in water is added and mixed with the polymer solution using a volume of the compound solution which does not materially reduce the solution viscosity (for example, a tenth volume). Typically, the digestion may be carried out at 20° C. to 30° C. Welan solutions serve as a convenient, positive control and xanthan solutions as negative control. Digestion of the unknown polymer by the inventive compound indicates that the polymer has a backbone structure similar to gellan. Of course, the unknown polymer may or may not have a side chain substitution on the glucose 2 residue of the backbone, and may have either rhamnose or mannose at the fourth position of the backbone subunit structure (residue X in structure I). The method provides a rapid, simple, and inexpensive screening with a small amount (less than one gram) of impure sample material.

The following examples illustrate the invention:

EXAMPLE 1:

Method of Selection of the Pure Strain, B2.9

EXPERIMENT 1A Enrichment

Damp soil was collected from Palomar Mountain, San Diego County, Calif. from a site within one yard from the outflow of household laundry grey water. One volume of a welan solution (0.2% w/v) was added to about ten volumes of moistened soil. After 4 days at 20°–24° C., about 5 g of soil were resuspended in 25 ml of deionized water (DI) and the solids were removed by centrifugation at 1000xG for 3 minutes. The supernatant was then centrifuged at 7000xG for 8 minutes to concentrate the microorganisms into a pellet and the pellet was resuspended in 1 ml of DI. Samples of 0.01 ml of this microbial suspension were spread on agar plates which contained welan as a major carbon source and P2 salts, $(NH_4)_2SO_4$ and plus 1000x trace minerals (described below). In addition, about 20 ml of welan-containing P2 salts medium were inoculated with the bacterial suspension and placed in a 125 ml shake flask.

Commercial welan contains some debris from the producing bacteria which can also serve as a nutrient source, and the agar is an additional carbon source in the plates.

COMPOSITION OF P2 SALTS 1 g $(NH_4)_2HPO_4$
2 g $K_2HPO_4$
0.5 g NaCl
0.05 g $MgSO_4\cdot7H_2O$
DI to 1 liter
pH was adjusted to 7.6

1000x Trace minerals:

0.5 g $ZnSO_4\cdot TH_2O$
0.5 g $FeSO_4\cdot7H_2O$
0.02 g $CuSO_4\cdot5H_2O$
0.02 g $NaMoO_4\cdot2H_2O$
DI to 100 ml Welan/P2 medium:

2.5 g welan
1.0 g $(NH_4)_2SO_4$
1 ml 1000x Trace minerals
P2 salts to 1 liter
(Add 15 g agar for plates)

After 3 days of incubation at 28° C., several colonial types were observed on the welan/P2 plates indicating that some bacteria might be using welan as a carbon source. Representative colonies were picked to fresh welan plates and again they grew.

After 6 days of shaking at 28° C. in welan/P2 medium without agar, the viscosities of the regrown welan/P2 liquid cultures were measured at about 25° C. at 6 rpm with a Brookfield LVTDV-II viscometer and spindle 18 and were as follows:

| | |
|---|---|
| With no bacteria | 41 cp |
| With soil bacteria | 6 cp |

These results show that microorganisms capable of degrading welan were present in the soil sample.

EXPERIMENT 1B *Gelrite TM Screen*

In order to screen for microorganisms capable of the endolytic digestion of welan, individual colonies from the welan/P2 plates and samples from the welan/P2 liquid culture were spread onto plates containing a chemically processed form of gellan. This processed gellan, in the form of commercial "Gelrite TM" (from Schweizerhall, Inc., 3001 Hadley Rd., South Plainfield, N.J.), lacks glycerate and acetyl substituents, forms gels in the presence of cations, and is a substitute for agar in solid microbiological media. Gelrite TM forms a transparent gel and is low in contaminating carbon and nitrogen materials, as compared to welan. Therefore, Gelrite TM can be used, not only as a sole carbon source, but also, as a solidifying agent for the plating medium, in the absence of agar or the contaminating carbon sources present in commercial welan. Gelrite TM and Gelrite TM /welan solid media are described below.

Microorganisms were selected for their ability to grow in solution with welan as the major carbon source and for their ability to create visible depressions on Gelrite TM plates. One microbial isolate that grew on welan-containing plates was purified on Gelrite TM and on Gelrite TM /welan plates. This isolate was capable of pitting the surface of both Gelrite TM and Gelrite TM /welan plates.

This microbial isolate reduced the viscosity of welan in solution as a pure culture as demonstrated by the following procedure:

In this experiment; 20 ml of welan medium was inoculated from a single microbial colony growing on a Gelrite TM plate. After 6 days incubation at 28° C. in welan/P2 medium without agar with shaking (250 RPM), the solution viscosity had decreased by about 80% and the mass of alcohol-precipitable welan had decreased 80%. Because of this result, this microbial pure strain was selected for further characterization, and designated bacterial strain B29. This strain has been deposited in the name of Shin-Etsu Bio, Inc., on Feb. 4, 1992, with the American Type Culture Collection, in Rockville, Md., and assigned Deposit No. ATCC 55294. This deposit has been made pursuant to the provisions of the Budapest Treaty on the International Recognition of the Deposit of Microorganisms for the Purposes of Patent Procedure and all restrictions on the availability to the public of the materials so deposited will be irrevocably removed upon the granting of a patent thereon.

Gelrite TM plates: 10 g Gelrite TM
1 g $MgSO_4\cdot7H_2O$
2 g $(NH_4)_2SO_4$
1 g NaCl

|                        |                                                      |
|------------------------|------------------------------------------------------|
|                        | 0.02 M Sodium phosphate buffer pH 7.0                |
|                        | 1 ml 1000x trace minerals                            |
|                        | DI to 1 liter                                        |
| Gelrite TM /           | 1 l Gelrite TM plates plus 1 g welan                 |
| welan plates:          |                                                      |

EXAMPLE 2:

Identification of the microbial pure culture Strain B29

The standard tests for identification and results obtained are tabulated below. The standard tests were carried out as described in: *Color Atlas and Textbook of Diagnostic Microbiology*, E. M. Koneman et al. eds., J. B. Lippincott Company, Philadelphia, 1988; *Bergey's Manual of Systematic Bacteriology*, N. R. Krieg ed., Williams and Wilkens, Baltimore, 1984.

Colony morphology: Luria broth plate:
  2–3mm round; raised pinkish center adheres to agar; sticky.
  Gelrite TM plate: as above but creates depression; with adherent sticky consistency.

Microscopy:
  cells: in Luria broth (length=3xwidth); single or end-to-end pairs; rod-shaped.
  spores: oval; swell sporangium; subterminal.

Kligler iron agar:
  acid slant; no change in butt; no gas; no $H_2S$ from thiosulfate; glucose and lactose utilized on slant; aerobic growth only.

| Other tests:                            |                       |
|-----------------------------------------|-----------------------|
| Methyl red/Voges-Proskauer:             | −/−                   |
| Catalase:                               | −                     |
| Oxidase:                                | borderline or delayed |
| Indole:                                 | −                     |
| Lysine decarboxylase:                   | −                     |
| Arginine dihydrolase:                   | −                     |
| Ornithine decarboxylase:                | −                     |
| Growth on TCBS plates:                  | −                     |
| Growth MacConkey's agar:                | +                     |
| Growth in LB plus 6% NaCl:              | −                     |
| Growth in LB plus KCN (0.0075% w/v):    | −                     |
| Growth in LB plus ampicillin (30 μg/ml):| +                     |
| Growth in LB plus vancomycin (20 μg/ml):| −                     |
| Growth in LB plus polymyxin (10 μg/ml): | +                     |
| KOH:                                    | Viscous in 3% w/v −   |
| Hydrolysis of arbutin:                  | −                     |
| Hydrolysis esculin:                     | +                     |
| Hydrolysis elastin:                     | −                     |
| Hydrolysis gelatin:                     | +                     |
| Hydrolysis starch:                      | +                     |
| Hydrolysis casein:                      | +                     |

| Utilization of carbon sources: | | |
|----------|----------|-----------------|
| Compound | Growth   | Acid production |
| arabinose | + | + |
| fructose  | + (thin) | + |
| galactose | + | + |
| glucose   | + | + |
| lactose   | + | + |
| maltose   | + | + |
| mannose   | + | + |
| raffinose | + | + |
| rhamnose  | + (thin) | + |
| salicin   | + | + |
| sucrose   | + | + |
| lysine    | − | |
| arginine  | − | |
| ornithine | − | |
| histidine | − | |
| citrate   | + (thin) | |

The results of these tests show that the biologically pure culture isolate B29 was a gram-positive aerobic spore-former, and thus, a *Bacillus* species. Among the *Bacillus* species listed in the 1984 Bergey's Manual, isolate B29 most closely matched *Bacillus brevis*. The only discrepancies were that *B. brevis* usually does not make acid from arabinose and usually is catalase positive. We therefore refer to B29 as a *Bacillus* species.

EXAMPLE 3:

Induction of accumulation of an extra-cellular welan-degrading activity.

In order to test whether or not welan could serve as a specific inducer of the synthesis and secretion of a welan-degrading activity, two different liquid media were inoculated with B29 bacteria: one contained welan and the second contained xanthan. Like welan, xanthan is a negatively charged, high viscosity carbohydrate polymer, but xanthan has no sugar linkages in common with welan. The two media included 0.4% (w/v) ammonium sulfate, 0.2% (w/v) sodium chloride, 0.2% (w/v) magnesium chloride, 1x trace minerals as described above, and 0.25% (w/v) as either welan or xanthan. After 4 days incubation at 28° C. with shaking both media showed reduced viscosity, as seen by swirling the flasks and observing the resistance to flow. The cultures were centrifuged to remove the bacteria and sodium azide was added to a final concentration of 0.01% (w/v) to prevent metabolism by any residual bacteria. The clarified supernatants were then incubated with a sterile solution of autoclaved welan to detect welan-degrading compound.

As shown in Table 1, the supernatant from the growth of B29 bacteria on welan exhibited enzymatic activity which caused a rapid decrease in the viscosity of welan. The B29 bacteria also grew in medium containing xanthan as the principal source of carbon, but the culture supernatant did not degrade welan. This result indicated that the welan-degrading compound produced by the B29 bacteria was specifically induced by welan.

TABLE 1

| DIGES-TION TIME (HOURS) | VISCOSITY (cp) SAMPLE TESTED* | | |
|---|---|---|---|
| | WATER | XANTHAN SUPERNATANT | WELAN SUPERNATANT |
| 0 | 93 | 97 | 96 |
| 1 | 86 | 88 | 23 |
| 2 | 84 | 90 | 18 |
| 3 | 82 | 91 | 12 |

*5 ml of culture supernatant or water were mixed with 5 ml of 0.2% (w/v) welan in water.

EXAMPLE 4:

Purification and concentration of Welan-degrading compound

The welan-degrading compound was purified and concentrated by methods commonly used to purify and concentrate proteins. The pure B29 strain was inoculated into 200 ml of M9 minimal salts medium containing 0.125% (w/v) welan and allowed to grow for 4 days with shaking (200 rpm) in a baffled 500 ml flask at 28° C. M9 minimal salts is composed of (per liter):

6 g Na$_2$HPO$_4$,
3 g KH$_2$PO$_4$,
0.5 g NaCl,
1 g NH$_4$Cl,
includes 10 ml of a 0.01 M solution of CaCl$_2$ and 1 ml of a 1M solution of MgSO$_4$-7H$_2$O added after autoclaving.

The culture broth was centrifuged (11,000xG for 10 min) and filtered through Whatman number 1 paper to remove cells and debris. Different amounts of ammonium sulfate were added to each of five samples (20 ml) of the cell-free extract to precipitate the compound. The ammonium sulfate was added slowly over a period of about 30 minutes to give final amounts ranging from 0 to about 86% of saturation at room temperature and each sample was held for 10 minutes at room temperature before proceeding. The solutions were centrifuged at 11,000xG for 10 minutes to separate the insoluble proteins in the precipitate from the soluble proteins in the supernatant. The precipitated proteins were resuspended in 5 ml DI and then the precipitates and supernatants were placed separately in porous cellulose-ester dialysis bags that have a molecular weight cut-off of 6,000 to 8,000 Daltons and dialyzed against DI.

Enzymatic activity was determined by measuring viscosity after digestion of a solution of welan (0.625 mg/ml in 20 mM of sodium phosphate buffer at pH 7). The viscosity was plotted as a function of time and then the relative enzyme activity was calculated as the absolute value of the slope. The results are set forth in Table 2.

TABLE 2

| AMMONIUM SULFATE | ENZYMATIC ACTIVITY (cp/hr) | |
|---|---|---|
| (% SATURATION) | SUPERNATANT | PRECIPITATE |
| 0 | 10 | 0 |
| 18 | NT* | 0 |
| 34 | 16 | 0 |
| 61 | 0 | 10 |
| 86 | 0 | 12 |

*NT, not tested.

These results show that most of the compound was precipitated in ammonium sulfate at about 61% saturation and was soluble in ammonium sulfate at 34% saturation. Based on these results, the compound was purified and concentrated from the cell-free culture broth by first adding ammonium sulfate to 34% of saturation and removing and discarding the precipitated material by centrifugation. The supernatant fraction was then brought to 55% of saturation of ammonium sulfate and the resulting precipitate was recovered by centrifugation. The second precipitate was re-dissolved, dialyzed and used as purified, concentrated compound, e.g., in Example 6. The first precipitate in ammonium sulfate at 34% of saturation contained a minor fraction of the total compound while the second precipitate in 55% of saturation of ammonium sulfate contained the major portion of the compound.

EXAMPLE 5:

The Inventive Compound is an Endoglycanase.

An experiment was carried out wherein welan was digested using the inventive compound and samples of the digestion mixture were measured on a periodic basis to determine the viscosity and amount of reducing sugars present. In the experiment, the purified and concentrated compound prepared in Example 4 was used to digest welan in solution. The digestion mixture contained welan (0.06% w/v, final concentration), a solution of the inventive compound (25% of final volume), and 0.013 M sodium phosphate buffer at pH 7. Samples (0.5 ml) were taken periodically and high molecular weight welan was removed by precipitation by the incremental addition of isopropyl alcohol (IPA) to the sample until a final concentration of IPA of about 66% (v/v) was reached, followed by centrifugation. The unprecipitated low molecular weight material released during digestion was recovered from the IPA by evaporation. The amount of reducing sugars in the samples was measured using the assay described in Starch and Its Derivatives, 1968, J. A. Radley, pp.432–433. The results are set forth in Table 3. As shown, no detectable release of reducing sugars was observed until late in the digestion period. However, the viscosity of the welan decreased within a relatively short period of time after the start of the digestion. This rapid loss of viscosity and concomitant slow release of reducing sugars indicates that the inventive compound is an endoglycanase, since an exolytic enzyme would have released reducing sugars at an earlier stage of the digestion.

TABLE 3

| DIGESTION TIME (HOURS/MINUTES) | VISCOSITY (cp) | REDUCING SUGARS (Absorbance, 520 nm) |
|---|---|---|
| 0/10 | 83 | 0 |
| 0/30 | 71 | 0 |
| 1/0 | 61 | — |
| 1/30 | 52 | — |
| 2/0 | 42 | — |
| 2/20 | 38 | 0 |
| 4/0 | 31 | 0 |
| 5/0 | 20 | — |
| 6/40 | 12 | 0 |
| 21/30 | 5.3 | 0.039 |
| 24/0 | 3.6 | 0.047 |
| 29/0 | 0 | 0.061 |
| 45/0 | 0 | 0.105 |
| 53/0 | 0 | — |
| 120/0 | 0 | 0.227 |

EXAMPLE 6:

Enzyme Action on Gelrite TM gels.

The purified compound prepared as in Example 4 was capable of rapidly digesting Gelrite TM gels. A drop (about 8 mm in diameter containing 0.01 ml) of the purified compound was placed on the surface of a Gelrite TM gel solidified in a plastic dish. Within 30 minutes at 28° C., a hole about 8 mm in diameter and 0.5 mm deep was formed on the surface of the gel. The digestion was continued for 24 hours and the depth and width of the hole in the gel increased to about 12 mm in diameter and 3–4 mm deep.

EXAMPLE 7:

Production of Low Viscosity Welan Using the Inventive Enzyme.

Crude cell-free product was prepared by diluting a liquid culture of bacteria B29 (prepared as in Example 4) with an equal volume of DI and crude commercial welan (dry powder) was allowed to hydrate in this enzyme solution at 5% (w/v) with sodium azide added to prevent microbial growth. The solution was highly viscous with a semi-solid, pudding-like consistency and would not pour from the beaker. Digestion was allowed to proceed at 28° C. When digestion was terminated, the welan solution contained less than 400 viable cells per ml. At intervals, samples of the digestion mixture (2 g) were removed, diluted 10-fold with DI (to a final weight of 20 g) and the viscosity was measured. The welan was then precipitated from this sample by addition of IPA, as described in Example 5. The precipitate was recovered by centrifugation and dried to constant weight to determine the amount of welan that remains precipitable during the course of digestion. As shown in Table 4, the viscosity of the welan solution declined over a period of days to produce a solution of low viscosity material. These results demonstrate that the crude compound was able to digest a concentrated welan solution and to remain active for at least 7 days of incubation under these conditions.

In addition, these data further confirm the endolytic activity of the inventive compound. Although the mass of high molecular weight welan decreased slowly during the course of the digestion. There was a rapid decline in viscosity. These results indicate endolytic digestion, as compared to exolytic digestion, where viscosity loss would be much slower and would parallel the decrease in the mass of IPA-precipitable polymer.

TABLE 4

| DIGESTION TIME (HOURS) | VISCOSITY (cp) | WELAN (mg) (IPA-PRECIPITATE) |
|---|---|---|
| 0 | 1820 | 71 |
| 28 | 524 | 66 |
| 46 | 160 | 62 |
| 70 | 52 | 57 |
| 77 | 45 | 54 |
| 140 | 9 | 49 |
| 164 | 0 | 47 |

EXAMPLE 8:

Enzyme Activity of the Inventive Compound on Various Polysaccharides having Common Backbone Structures.

Solutions of polysaccharides with different primary structures were prepared. These included the structurally related polymers of the "gellan family" (gellan, Gelrite TM, welan, rhamsan, S-88 and S-198) and polymers with unrelated structures (B-1973, K-54, and xanthan). In addition, one polysaccharide (S-7) was prepared.

Crude polysaccharides (gellan, rhamsan, S-88, S-7, S-198, B-1973, K-54) were prepared by growing the appropriate producing strain. All bacterial strains were grown in liquid culture (approximately 50 ml in baffled 250 ml flasks) with shaking (about 200 rpm) at room temperature for from 3 to 7 days, depending on the rate of accumulation of polymer. The cultures were precipitated with 3 volumes of IPA, the precipitates were recovered (manually by spooling or by centrifugation), the excess IPA was pressed from the precipitate, and the polymer was dissolved in DI.

Samples of Gelrite TM were obtained from Schweizerhall and welan and xanthan gum were obtained from Kelco. The initial viscosities of the polysaccharide solutions were measured at 6 rpm with spindle #18 of a Brookfield LVTDV-II viscometer at room temperature. Sufficient polymer was added to the test solutions so that the initial viscosities were in the range of 70 cp (for K-54) to 14 cp (for S-198). Purified compound was prepared as described in Example 4, and 0.2 ml of the compound was mixed with 8 ml of each polysaccharide.

| POLYMER | ATCC NUMBER | GROWTH MEDIA |
|---|---|---|
| Gellan | 31461 | YMP + 3% sucrose |
| Rhamsan | 31961 | YMP + 3% sucrose |
| S-88 | 31554 | YMP + 3% sucrose |
| S-7 | 21423 | YMP + 2% sucrose |
| S-198 | 31853 | YMP + 3% glucose |
| B-1973 | 19584 | CM |
| K-54 | 12658 | CM |

| YMP MEDIUM | |
|---|---|
| | per Liter |
| Bacto Yeast Extract | 3 g |
| Malt Extract | 3 g |
| Bacto Peptone | 5 g |
| Bacto Agar (as per Difco Manual) | 20 g |

| CM MEDIUM |
|---|
| 1% Tryptone |
| 0.2% Yeast Extract |
| 0.2% Casamino Acids |
| 0.5% Glucose |
| P2 salts |

First and second sets of samples were digested for four days and 24 hours, respectively, at 22°–24° C., after which the viscosities of each of the samples were measured using the procedure outlined above. The results of the two digestions are set forth in Table 5.

In summary, the enzyme digested Gelrite TM, welan, Si198, and S-88 among the gellan family of related polymers, and did not digest B-1973, K-54 or xanthan.

As demonstrated in Example 6, the inventive compound digested the Gelrite TM form of gellan as shown by the liquification of the Gelrite TM gels. However, the native form of gellan secreted by the producing bacteria resists digestion. Gelrite TM is produced by the chemical treatment of gellan which removes the glycerate attached to glucose 1 of each subunit (Kuo, M. -S., and A. J. Mort, 1986, Carbohydrate Research 156, 173–187). The inventive compound endolytically cleaves those polysaccharides having the gellan subunit structure wherein the glucose 1 residue is free of substitution. Thus, native gellan is resistant to digestion with the compound, while the chemically processed Gelrite TM is digested. Similarly, rhamsan is resistant to the compound due to the substitution of the glucose 1 residue with a side chain consisting of two glucose residues.

TABLE 5

| | | Digestion by enzyme | | |
|---|---|---|---|---|
| | | | Viscosity Change (%) | |
| Gellan Family Polymers | | Digest | First | Second |
| Names | Subunit Structure | yes/no | Set | Set |
| gellan S-60 | GlcGlaGlcRha ↑ Gly | no | +14 | −19 |
| Gelrite TM | GlcGlaGlcRha | yes (1) | not applic. | not applic. |
| welan S-130 | GlcGlaGlcRha ↑ —(Rha/Man) | yes | −95 | −77 |

TABLE 5-continued

| Gellan Family Polymers | | Digest yes/no | Digestion by enzyme Viscosity Change (%) | |
|---|---|---|---|---|
| Names | Subunit Structure | | First Set | Second Set |
| S-88 | GlcGlaGlc(Rha/Man)<br>↑<br>Rha | yes | −93 | −42 |
| S-7 | (GlcGlaGlcRha)(2)<br>↑<br>GlcGlc | yes | −74 | not done |
| S-198 | GlcGlaGlc(Rha/Man)<br>↑<br>Rha(0.5) | yes | −44 | −40 |
| rhamsan S-194 | GlcGlaGlcRha<br>↑<br>GlcGlc | no | −17 | −4 |
| Non-gellan polymers | | | | |
| B-1973 | MnaGlcGal | no | −24 | not done |
| K-24 | GlcGlaFuc<br>↑<br>Gal | no | −11 | not done |
| xanthan gum | GlcGlc<br>↑<br>ManGlaMan | no | −14 | −8 |

Abbreviations:
Glc glucose
Gla glucuronic acid
Rha rhamnose
Gly glycerate
Man mannose
Mna mannuronic acid
Gal galactose
Notes to Table 5:
(1) Liquification of Gelrite ™ gel. See Example 6 above.
(2) Hypothetical structure based upon approximate sugar composition (see U.S. Pat. No. 3,960,832), specificity of the welanase enzyme and analogy to S-194 structure.

An intermediate rate of digestion was observed for polysaccharide S-198. The reported structure of S-198 (Chowdhury, T. A., B. Lindberg, U. Lindquist, and J. Baird, 1987, *Carbohydrate Research* 161,127–132) indicates that, on the average, the glucose 1 residue of the subunit structure is half-substituted with rhamnose. Therefore, S-198 may be a single polysaccharide structure with side chain substitution on each second backbone subunit or, alternatively, it may be a mixture of two different structures: an unbranched gelrite-like polysaccharide and a fully-substituted polymer with the structure reported for S-198. However, the latter possibility was eliminated by use of the inventive compound. When S-198 was digested with the compound for a sufficient period of time, essentially all viscosity of the S198 solution was lost indicating that all of the polymer chains are susceptible to digestion by the compound. The slow rate of digestion of S-198 appears to be due to the partial substitution of the glucose 1 residue of the subunit structure of a single type of polymer. These results demonstrate that the compound can be used to distinguish between two alternative polysaccharide structures, i.e., a mixture of two polymer structures and a partially substituted, single polymer type.

The composition of S-7 is reported in U.S. Pat. No. 3,960,832, as glucose (73%), rhamnose (16%) and glucuronic acid (11%). This sugar composition is similar to the composition reported for rhamsan (U.S. Pat. No. 4,401,760), which contains glucose (73–77%), rhamnose (20–21%) and glucuronic acid (9%). Polysaccharide S-7 was digested by the compound which indicated that it is a member of the gellan family. Within this family, there are pairs of polysaccharides which differ only in the location of the side chain. For example, S-88 has a monosaccharide rhamnose side chain on the glucose 2 of the subunit structure, while S-198 has a monosaccharide rhamnose attached to glucose 1. Therefore, S-7 and S-194 appear to represent such a structurally related pair: S-194 has a side chain of two glucose residues attached to glucose 1 of the subunit structure and S-7 appears to have the same side chain attached to the glucose 2.

These results show that the enzyme activity of the inventive compound is specific for a subset of polysaccharides within the gellan family.

EXAMPLE 9

Soil samples were obtained from the location described in Example 1, but about 6 months after these first samples. Three soil samples (about 25 g) were incubated with 5 ml of a 0.25% aqueous solution containing welan, xanthan gum, or no polysaccharides for purposes of enrichment. The samples were incubated at room temperature for 5 days. Aliquots of about 10 ml volume were removed from each sample, 20 ml of DI were added and the suspension was incubated for 2 hours at 28° C. with shaking. These samples were then centrifuged to remove soil particles and the supernatant was filtered through Whatman filter paper. The clarified supernatant was then diluted and plated on a rich medium (YM medium) to estimate the approximate total number of bacteria and on Gelrite ™ plates to estimate the number of bacteria capable of growing on Gelrite ™. The number of "pit forming" colonies on Gelrite ™ plates indicate the number of bacteria capable of endolytic digestion of Gelrite ™ and the results are shown in Table 6.

The enrichment of the soil samples with welan results in numerous colonies that grow on Gelrite ™. Approximately 7% of the total bacteria recoverable from the soil are Gelrite ™ digestors in the welan-enriched samples, whereas about one in 20,000 (0.005%) of the total bacteria exhibited this activity in the soil samples enriched with xanthan gum, an unrelated polysaccharide. It was observed that while most of bacterial colonies that grew on Gelrite ™ plates formed pits on the gel surface, approximately 30% of the total colonies growing on the surface did not form pits. Presumably these colonies represented bacteria capable of obtaining sugars from Gelrite ™ by an exo-digestion process but having limited or no endolytic activity.

TABLE 6

| BACTERIAL COLONIES (100 FOLD DILUTION) | | |
|---|---|---|
| POLY-SACCHARIDE | TOTAL BACTERIA (YM PLATES) | NO. FORMING PITS (Gelrite ™ PLATES) |
| NONE | 1,700 | 0 |
| WELAN | 56,000 | 4,000 |
| XANTHAN | 20,800 | 1 |

EXAMPLE 10:

An additional experiment to produce and purify the extracellular welandegrading compound of the invention was carried out. For this purpose, Strain B29 was grown at 30° C. for 120 hours by shaking in Erlenmeyer flasks containing P2 salts and 0.25% welan. The culture broth (1875 ml) was centrifuged (10,000xG for 15 minutes) to remove cells therefrom and then sodium azide was added to a concentration 0.01%.

Solid ammonium sulfate was added to 34% of saturation and the mixture was allowed to sit at 4° C. for 30 minutes. The precipitate was removed by centrifugation for 15 minutes at 10,000xG. Solid ammonium sulfate was added to the supernatant to 64% of saturation.

The compound in the supernatant was then precipitated by incubation at 4° C. for 30 minutes and centrifugation at 10,000xG for 15 minutes. The active pellet obtained was resuspended in deionized water and dialyzed overnight at 4° C. against water. Some insoluble material was removed by centrifugation at 10,000xG for 15 minutes. Thereafter, the soluble fraction was further purified by making it 25 mM with NaCl and then loaded onto an anion-exchange chromatography column containing DEAE-Sepharose CL-6B from Sigma. The column was maintained at room temperature.

The proteins were first eluted by washing with 50 mM NaCl in 20 mM Tris-HCl at pH 7.6, and thereafter with a gradient of buffered NaCl to 500 mM.

A separate sample was used for hydrophobic interaction chromatography by loading it onto a column of octyl-Sepharose (Sigma) in 1M NaCl and 20 mM Tris-HCl at pH 7.6 and thereafter, the proteins were eluted with a gradient of buffered NaCl to 0M.

Another sample was subjected to gel filtration chromatography by applying a concentrated sample to a column of Sephacryl 400-HR (Sigma) in 150 mM NaCl and 20 mM TrisHCl at pH 7.6. The proteins were then eluted with the same liquid. The elution of the enzyme as monitored by spotting samples of each fraction onto Gelrite TM plates and the active fractions were pooled. The enzyme compound was also separated from other proteins by electrophoresis through non-denaturing submerged 1.4% agarose gels with a constant recirculation of the buffer, 50 mM MOPS pH 7.5. The rate of migration for the inventive enzyme toward the anode was almost as fast as for bovine serum albumin. In contrast, egg white lysozyme moved toward the cathode. Pieces of the gel were excised and the proteins were eluted by diffusion into 50 mM MOPS at pH 7.5 buffer.

The addition of welan to the medium to stimulate the synthesis of the inventive enzyme also adds bacterial protein and cell debris from the polysaccharide-producing microorganism. As a result, even though the enzyme was secreted into the medium, it became mixed with contaminating proteins. Nevertheless, the enzyme properties before and after purification were characterized and found to be the same. Table 7 summarizes the purification results. It is noted that the initial step is to concentrate the enzyme about 100-fold from the culture broth by precipitation with high concentrations of ammonium sulfate. This removes about one half of the protein and about one half of the enzyme activity is recovered.

TABLE 7

| Fraction | Volume (ml) | Total Units* | Total Protein (mg) | Sp Act (U/mg) |
|---|---|---|---|---|
| Culture supernatant | 1630 | 7063 | 142 | 50 |
| (NH4)N2SO4 precipitate | 13 | 7248 | 64 | 113 |
| DEAE-Sepharose pool | 13 | 1681 | 7 | 244 |

*One unit of enzyme activity is the amount of enzyme that reduces the viscosity of 0.1% welan (in 50 mM MOPS pH 7.5) by 1 centipoise (cp) per minute, when reacted at 40° C. and measured with a Brookfield LVTDV-II viscometer with spindle 18 rotating at 1.5 rpm.

We discovered that the enzyme activity behaved as an acidic protein at neutral pH since its electrophoretic mobility in non-denaturing agarose gels is similar to that of bovine serum albumin which has an isoelectric point of 4.8.

Because of this property, a second purification step of iron exchange chromatography through DEAE-Sepharose with elution with increasing amounts of NaCl was carried out. About one half of the material absorbing at 280 nm did not bind to the matrix and one-fourth eluted above 500 mM NaCl. The one-fourth eluate included charged polysaccharides, most likely, residual welan from the medium. The enzyme activity eluted as a single peak with 200 to 300 mM NaCl. The pool of the active fractions contained about one-fourth of the protein loaded and about three-fourths of the enzyme activity. Upon separation of the proteins by electrophoresis through denaturing SDS polyacrylamide gels and stained with Coomassie Brilliant Blue R250, one polypeptide of about 110,000±10,000 daltons was prominent with about six other faint bands.

The gel filtration through Sephacryl 400HR or hydrophobic interaction chromatography removed some of the hinter polypeptide species. While the recovery of the inventive enzyme activity was low, especially from octyl-Sepharose, after electrophoresis of a sample of the DEAE pool through an agarose gel at pH 7.5, and slicing and elution of the protein with 50 mM MOPS pH 7.5, the active fractions were determined by spotting on a Gelrite gel and analyzed with an SDS polyacrylamide gel. The active polypeptide corresponded with the 110,000 dalton species.

Additional electrophoresis of a portion of a DEAE pool and agarose gel, showed that a single polypeptide of about 110,000±10,000 daltons exhibited the inventive enzymatic activity.

A series of tests were carried out to determine the optimum pH range or activity of the inventive enzyme using a variety of buffers. In addition, the inactivation temperature for the inventive enzyme and the optimum reaction temperature for the enzyme were also determined. Based on this analysis, the most useful pH range for the inventive enzyme is from about 4.5 to 9, preferably, from about 6.5 to 8, and most preferably, from 7.2 to 7.8. The inventive enzyme is most desirably used at temperatures between 10° and 60° C. as it is most active in this range. Preferably, the enzyme is used in the range from about 30° to 50° C. At temperatures below 30° C., the activity becomes more sluggish and at temperatures above 50° C., the enzyme becomes inactivated by heat.

Table 8 shows the results of an experiment using a variety of buffers to determine optimum pH for the hydrolysis of welan by the inventive enzyme. These experiments were carried out using a solution of 0.1 percent welan and the inventive enzyme from the DEAE pool fraction. Buffers used were acetate, citrate, phosphate, MOPS, and Tris. The buffer was present at a final concentration of 50 mM. The activity was measured by determining the viscosity using a temperature-jacketed spindle #18 and a Brookfield LVTDV-II viscometer.

TABLE 8

| Buffer | pH | Initial Reaction (change in cp/min) |
|---|---|---|
| Acetate | 4.6 | 0.8 |
|  | 5.6 | 2.4 |
| Citrate | 5.0 | 0.0 |
|  | 6.0 | 0.5 |
| Phosphate | 6.0 | 5.9 |
|  | 6.9 | 7.0 |
|  | 7.9 | 5.7 |
| MOPS | 6.5 | 9.2 |
|  | 7.0 | 8.9 |
|  | 7.5 | 11.0 |
|  | 7.5 | 10.7 |
|  | 8.2 | 9.3 |
| Tris | 7.4 | 10.6 |
|  | 8.0 | 9.4 |
|  | 8.0 | 8.3 |
|  | 9.0 | 5.2 |

The initial reaction rate of the inventive enzyme after treatment at a given temperature, the results were determined. These results are shown in Table 9.

TABLE 9

| Inactivation Temperature (°C.) | Initial Reaction Rate (change in cp/min) |
|---|---|
| 40 | 11 |
| 45 | 11 |
| 50 | 7 |
| 60 | 0.1 |
| 80 | 0.2 |

Also, optimum reaction temperature for the inventive enzyme was measured and these results are shown in Table 10. For the results in the last two tables, the buffer was 50 mM MOPS at pH 7.5 and the substrate used was 0.1% welan.

TABLE 10

| Reaction Temperature (°C.) | Reaction Rate (change in cp/min) |
|---|---|
| 10 | 1.2 |
| 20 | 2.4 |
| 30 | 7.7 |
| 40 | 23 |
| 50 | 46 |
| 60 | 79 |

A test was also carried out to determine the ability of the inventive enzyme to digest various polysaccharides. Solutions of gellan related polysaccharides were prepared and the initial viscosities were measured. Thereafter, 0.05 to 0.2 ml of the inventive enzyme (the DEAE fraction) was mixed with 8 ml of the polysaccharide solution. The polysaccharides used were gellan, deacetylated gellan, welan, rhamsan, deacetylated rhamsan, S-88, S-198, deacetylated S-198, NW-11, and S-7. Polysaccharides with unrelated structures were also tested, namely, B-1973, K-54 and xanthan (Keltrol). After equilibrium of the temperature, the initial viscosities were measured and the inventive enzyme was mixed with the polysaccharide solution. The change in viscosity was monitored as a function of time at 40° C. Table 11 shows the results.

TABLE 11

| Substrate | Subunit Structure[a] | Reaction Rate[b] |
|---|---|---|
| Welan | Glc—GlcUA—Glc—Rha<br>↑<br>(Rha or Man) | 4.0 ± 0.3 |
| Gellan | Glc—GlcUA—Glc—Rha<br>↑<br>Glycerate | 2.6 ± 0.8 |
| S-198 | Glc—GlcUA—Glc—(Rha or Man)<br>↑<br>Rha(0.5) | 2.6 ± 0.4 |
| S-7 | unknown | 2.3 ± 1.1 |
| S-88 | Glc—GlcUA—Glc—(Rha or Man)<br>↑<br>Rha | 1.5 ± 0.5 |
| Rhamsan | Glc—GlcUA—Glc—Rha<br>↑<br>Glc—Glc | 0.2 ± 0.3 |
| NW11 | Glc—GlcUA—Glc—Man | 0.2 ± 0.1 |

As seen, the inventive enzyme exhibits activity towards welan, gellan, S-198, S-7, and S-88. It exhibits essentially no activity toward rhamsan, NW-11, B-1973, K-54 and xanthan. The inventive enzyme was also active against the chemically deacetylated forms of gellan, rhamsan and S-198 to essentially the same degree as the native polysaccharides, although this data is not shown in the Table.

What is claimed is:

1. A biologically pure culture of Bacillus ATCC 55294 which produces an endoglycanase having endolytic activity against polysaccharides having the subunit backbone structure;

$$\begin{array}{c} 1 \\ \rightarrow 3)\text{-}\beta\text{-D}-\text{Glc-}(1\rightarrow 4)\text{-}\beta\text{-D}-\text{GlcA-} \\ | \\ 2 \\ (1\rightarrow 4)\text{-}\beta\text{-D}-\text{Glc-}(1\rightarrow 4)\text{-}\alpha\text{-L}-\text{X-}(1\rightarrow \end{array} \quad (I)$$

wherein Glc is glucose, GlcA is glucuronic acid, Rha is rhamnose, Man is mannose, X may be Rha or Man, and wherein the reducing end of the polymer is toward the X residue of the backbone.

2. The culture of claim 1 which is capable of using a polysaccharide selected from the group consisting of gellan, Gelrite ™, welan, S-198, S-7 and S-88, deacetylated gellan, and deacetylated S-198, as a carbon source.

3. A biologically pure culture of Bacillus ATCC 55294 which produces an endoglycanase having endolytic activity against polyseccharides having the subunit backbone structure:

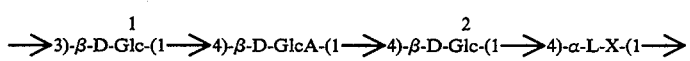

wherein Glc is glucose, GlcA is glucuronic acid, Rha is rhamnose, Man is mannose, X may be Rha or Man, and wherein the reducing end of the polymer is toward the X residue of the backbone, said Bacillus ATCC 55294 being obtained by:

a) subjecting a naturally occurring collection of bacterial straining to growth conditions in a medium containing a polysaccharide having the subunit backbone structure;

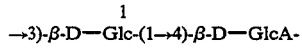

$$(1\rightarrow 4)\text{-}\beta\text{-D}\text{—Glc-}(1\rightarrow 4)\text{-}\alpha\text{-L}\text{—X-}(1\rightarrow$$

wherein the reducing end of the polymer is toward the Rha residue of the backbone, as the predominate carbon source;

b) selecting a colony of cells which grow under the conditions of step a);

c) subjecting the selected colony from step b) to plate growth conditions in a gel medium containing the polysaccharide having structure I as the predominant carbon source; and d) selecting a strain from step c) which causes pitting of the gel.

4. The culture of claim 3 wherein the polysaccharide used in step c) is deacetylated gellan.

5. The culture of claim 3 wherein the gel medium in step c) consists of the polysaccharide having structure (I).

6. The culture of claim 3 wherein the gel medium in step c) consists of deacetylated gellan.

7. The culture of claim 3 wherein the polysaccharide is selected from the group consisting of gellan, Gelrite ™, welan, S-198, S-7 and S-88, deacetylated gellan, and deacetylated S-198.

* * * * *